United States Patent [19]

Nakagawa et al.

[11] Patent Number: 5,352,437
[45] Date of Patent: Oct. 4, 1994

[54] FOAMABLE AEROSOL PREPARATION

[75] Inventors: Akira Nakagawa; Satoru Miyata; Kenji Masuda, all of Tosu, Japan

[73] Assignee: Hisamitsu Pharmaceutical Co., Inc., Tosu, Japan

[21] Appl. No.: 689,067

[22] PCT Filed: Jul. 23, 1990

[86] PCT No.: PCT/JP90/00944
§ 371 Date: Jun. 7, 1991
§ 102(e) Date: Jun. 7, 1991

[87] PCT Pub. No.: WO91/01712
PCT Pub. Date: Feb. 21, 1991

[30] Foreign Application Priority Data

Jul. 28, 1989 [JP] Japan .................. 1-197674

[51] Int. Cl.$^5$ .......................... A61K 7/00; A61K 9/12
[52] U.S. Cl. ........................................ 424/45; 424/47; 514/945
[58] Field of Search ........................ 424/45, 47, 11; 514/945

[56] References Cited

U.S. PATENT DOCUMENTS

| | | | |
|---|---|---|---|
| 3,705,855 | 12/1972 | Marschner | 252/90 |
| 3,728,265 | 4/1973 | Cella et al. | 252/90 |
| 4,574,052 | 3/1986 | Gupte et al. | 252/90 |
| 4,652,389 | 3/1987 | Moll | 252/90 |
| 5,160,665 | 11/1992 | Owada et al. | 252/307 |
| 5,223,244 | 6/1993 | Moro et al. | 424/46 |

Primary Examiner—Thurman K. Page
Assistant Examiner—Robert H. Harrison
Attorney, Agent, or Firm—Bucknam and Archer

[57] ABSTRACT

A foamable aerosol preparation for use as the base of cosmetics, quasi drugs, drugs, and so forth, which comprises 0.1 to 5 w/v % of a surfactant, 0.05 to 10 w/v % of a lower alcohol and/or a glycol, 3 to 25 w/v % of water, and 60 to 95 w/v % of n-butane gas. Despite of the use of n-butane gas as the propellant, this preparation foams very well and is excellent in cracking sound when applied to skin. Furthermore it is particularly useful from the viewpoint of environmental protection, because it is free from the problem of the depletion of the ozonosphere by virtue of the use of a liquefied petroleum gas as the propellant instead of fluorocarbon gas heretofore used.

10 Claims, 1 Drawing Sheet

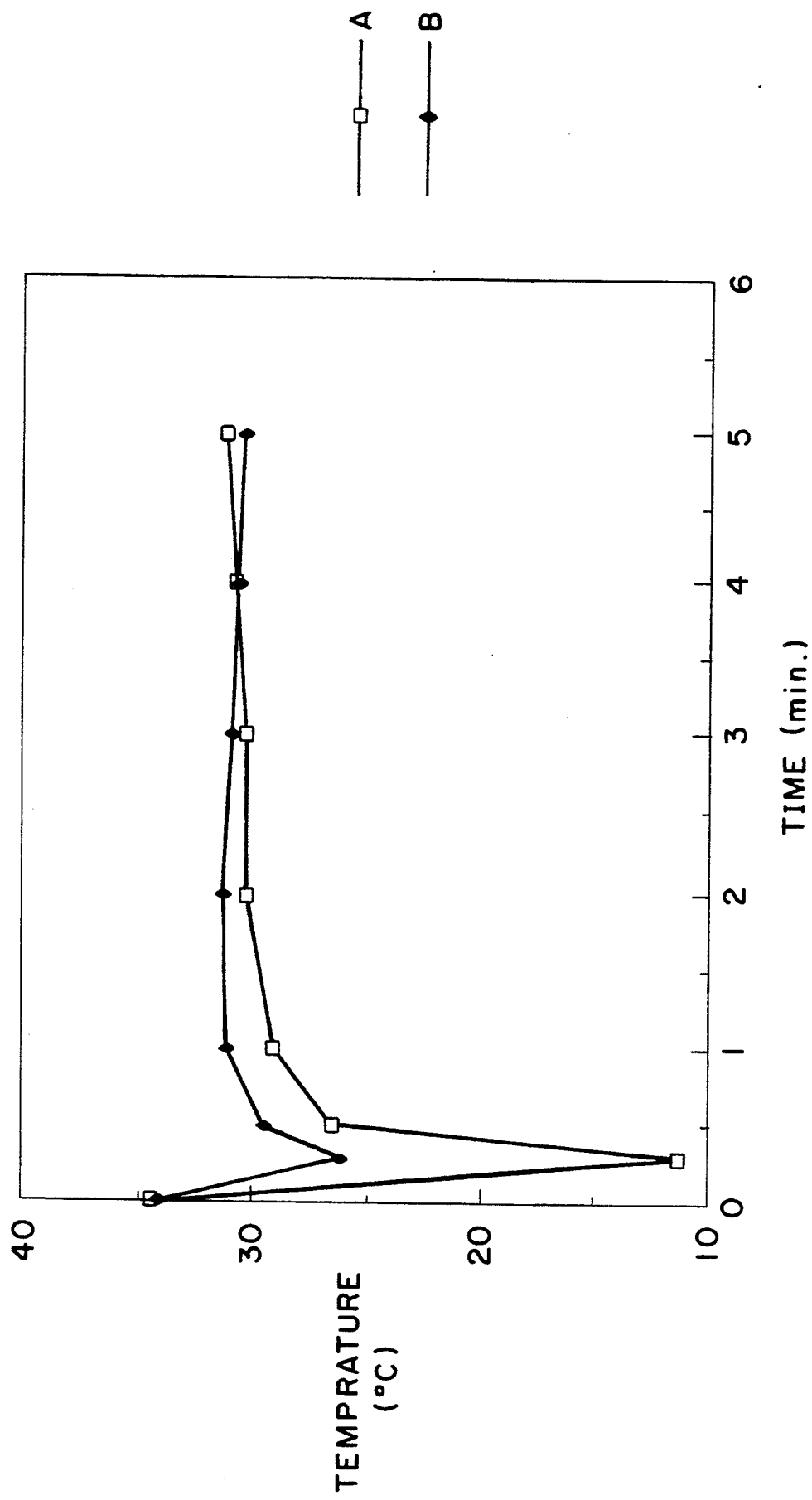

FOAMABLE AEROSOL PREPARATION

TECHNICAL FIELD

The present invention relates to a foamable aerosol preparation useful as cosmetics, quasi drugs and drugs and the bases thereof. More particularly, it relates to a cracking foam preparation which is one kind of the foamable aerosol preparations and which becomes foamed when applied to skin and makes cracking sound when rubbed by hands.

BACKGROUND ART

Cracking foam preparations have already been disclosed in, for example, Japanese Patent Application Publication Gazette No. (Sho.) 45-32053 and Japanese Patent Application Laid-Open Gazettes Nos. (Sho.) 63-141910, (Sho.) 63-141917 and (Sho.) 63-141917. Each of these cracking foam preparations employs a combination of a polyoxyethylene polyoxypropylene alkyl ether as an emulsifying agent and dichlorotetrafluoroethane (flon 114) as a propellant as a result of extensive studies on the emulsifying agent and propellant suitable for cracking foam preparations. This is because different combinations give preparations poor in the state of foaming and cracking sound and the use of flon 114 was not regulated at all at that time. Meanwhile, other studies have been made on the use of propane or isobutane alone or liquefied petroleum gas which is a mixture of propane, n-butane, isobutane and the like, as the propellant for cracking foam preparations. However, none of them could give a cracking foam preparation due to its low boiling point. The preparation of the present invention contains n-butane having a high boiling point as a propellant and is completely free from fluorocarbon gases and further it does not contain polyoxyethylene polyoxypropylene cetyl ether which is the most suitable emulsifying agent for flon 114. Thus, the preparation of the present invention is quite different from those of the prior art.

Recently, it has been found that fluorocarbon gases deplete the ozonosphere. Therefore, a worldwide agreement to regulate the use of fluorocarbon gases has been made from the standpoint of preventing environmental disruption and has come into effect in July, 1989. Further, the regulation of fluorocarbon gases will be tightened in the future, though stepwise, to finally abolish the use of fluorocarbon gases completely until the end of this century. Accordingly, it is an urgent requirement to develop a propellant for an aerosol preparation substituting fluorocarbon gases. However, the development of a propellant substituting flon 114 which is the most suitable gas for cracking foam preparations is so difficult that it is inevitable to use liquefied petroleum gas instead of flon 114. However, liquefied petroleum gas is too different from flon 114 in respect of physical properties such as specific gravity and boiling point to give a cracking foam preparation when the emulsifying agent according to the prior art is used. Particularly, when l-menthol, glycol salicylate or methyl salicylate is used as an active ingredient, no preparation acceptable in respect of both emulsifiability and cracking sound could be obtained due to an increased amount our the oil-phase components.

An object of the present invention is to provide a cracking foam preparation excellent in the state of foaming and cracking sound without using flon 114 as a propellant.

SUMMARY OF THE INVENTION

The inventors of the present invention have made extensive studies on cracking foam preparations using liquefied petroleum gas or the like as a propellant and have found that a gas containing as the major component n-butane having higher boiling point among the components of liquefied petroleum gas is essential to the preparation of a cracking foam preparation and that a cracking foam preparation excellent in the state of foaming and cracking sound can be obtained by using a specific amount of a surfactant in addition to the gas. The present invention has been accomplished on the basis of these findings.

The foamable aerosol preparation of the present invention is one comprising 0.1 to 5 wt./vol. % (the unit being hereinafter referred to as "w/v %") of a surfactant, 0.05 to 10 w/v % of a lower alcohol and/or a glycol, 3 to 25 w/v % of water and 60 to 95 w/v % of n-butane gas, and another which comprises a base comprising 0.1 to 5 w/v % of a surfactant, 0.05 to 10 w/v % of a lower alcohol and/or a glycol, 3 to 25 w/v % of water and 60 to 95 w/v % of n-butane gas, and an active ingredient added thereto.

At least one compound selected from the group consisting of polyoxyethylene alkylphenyl ethers, polyoxyethylene alkyl ether sulfates, polyoxyethylene alkyl ether acetates, polyoxyethylene alkylphenyl ether sulfates and polyoxyethylene alkylphenyl ether acetates is preferably used as the surfactant. The polyoxyethylene alkylphenyl ethers include polyoxyethylene nonylphenyl ethers and polyoxyethylene octylphenyl ethers, among which a polyoxyethylene octylphenyl ether having an HLB of 10 to 16 is particularly preferable. The polyoxyethylene alkyl ether sulfates or acetates and the polyoxyethylene alkylphenyl ether sulfates or acetates include sodium polyoxyethylene lauryl ether sulfate, sodium polyoxyethylene alkyl ether acetate, sodium polyoxyethylene nonylphenyl ether acetate, triethanolamine polyoxyethylene lauryl ether sulfate, ammonium polyoxyethylene lauryl ether sulfate, sodium polyoxyethylene alkyl ether sulfate, triethanolamine polyoxyethylene alkyl ether sulfate and sodium polyoxyethylene nonylphenyl ether sulfate, among which sodium polyoxyethylene lauryl ether sulfate is particularly preferable. These surfactants may be used alone or as a mixture of two or more of them depending upon the formulation. The surfactant is used in an amount of 0.1 to 5 w/v %, preferably 0.5 to 3 w/v %, in the foamable aerosol preparation of the present invention.

The lower alcohol includes ethanol and isopropanol, with the former being preferable. The glycol includes propylene glycol, 1,3-butanediol, 3-methyl-1,3-butanediol, dipropylene glycol, tripropylene glycol, glycerin, polyoxyethylene polyoxypropylene glycol and polyethylene glycol. These lower alcohols and glycols may be used alone or as a mixture of two or more of them, and used in an amount of 0.05 to 10 w/v %, preferably 0.1 to 7 w/v %, in the foamable aerosol preparation of the present invention. The water (purified water) is used in an amount of 3 to 25 w/v %, preferably 5 to 15 w/v %, in the preparation.

According to the present invention, n-butane is used as a propellant from the viewpoint of physical properties such as boiling point and specific gravity. The purity of n-butane gas is preferably 80 wt. % or higher, more preferably 90 wt. % or higher, most preferably 95 wt. % or higher. The amount of the n-butane gas used is 60 to 95 w/v %, preferably 70 to 90 w/v %. When this amount is less than 60 w/v %, the resulting preparation will be poor in cracking sound, though the state of foaming will be good. On the contrary, when it exceeds 95 w/v %, the resulting preparation will have too high a gas pressure to give an excellent state of foaming.

According to the present invention, an active ingredient such as an anti-inflammatory agent, antibacterial agent, hair-growth stimulant, antihistaminic (antiallergic agent) or insectifuge may be added in an amount of 0.0001 to 12 w/v %. The anti-inflammatory agent includes steroid type anti-inflammatory agents such as dexamethasone, prednisolone, diflucortone, fluocinonide, diflorasone diacetate, clobetasol propionate and Halcinonide; non-steroid type anti-inflammatory agents such as methyl salicylate, glycol salicylate, ketoprofen, indometacin, flurbiprofen, felbinac, sulprofen, piroxicam, fentiazac, pranoprofen, bendazac, bufexamac, ibuprofen piconol, felbinac ethyl, Loxoprofen, naproxen, oxaprozin, alminoprofen and tiaprofen; and local irritants such as l-menthol, peppermint oil, camphor, nonylic acid vanillylamide, capsaicin, benzyl nicotinate and methyl nicotinate. The antibacterial agent includes isopropylmethylphenol, chlorhexidine hydrochloride, clotrimazole, tolnaftate, bifonazole, econazole nitrate, omoconazole nitrate, miconazole nitrate, ketoconazole nitrate, isoconazole nitrate and oxiconazole nitrate. The hair-growth stimulant includes estradiol, ethinylestradiol, benzalkonium chloride, pantothenyl alcohol, hinokitiol, benzyl nicotinate, photosensitizer and Vitamin E. The antiallergic agent includes diphenhydramine, ketotifen, azelastine, salts of the azelastine, oxatomide, tranilast, chlorphenylamine maleate and sodium chromoglycolate. The insectifuge includes deer, turpentine oil and pyrethroid type agents.

In addition to the above essential components, the foamable aerosol preparation of the present invention may contain, as an oil-phase component, a fatty acid ester such as isopropyl palmitate, isopropyl myristate, diisopropyl sebacate, diethyl sebacate, diisopropyl adipate, glycerol caprylate or glycerol caprylate; a higher alcohol such as 2-octyldodecanol, 2-hexyldecanol or oleyl alcohol; a hydrocarbon such as squalane, liquid paraffin or isoparaffin; and a solubilizing agent such as crotamiton or benzyl alcohol. Further, the preparation may contain a powdery material such as talc, powdered silicon, powdered polystyrene or silica in order to improve the touch thereof.

A process for preparing the cracking foam preparation of the present invention will be described. The cracking foam preparation of the present invention can be prepared by feeding an oil-phase component or an active ingredient, and various additives including a surfactant, a lower alcohol and/or a glycol and water into a pressure vessel, setting a valve on the vessel, injecting a propellant (n-butane gas) into the vessel under pressure, heating the vessel to room temperature or a temperature of up to 60° C. and shaking the vessel at that temperature.

BRIEF DESCRIPTION OF DRAWING

FIG. 1 shows the results of Experiment 2 on the skin temperature change of a healthy adult man, wherein curve A refers to a case of the cracking foam preparation of Example 5 while curve B refers to a case of the aerosol preparation of Referential Example 5.

BEST MODE FOR CARRYING OUT THE INVENTION

The present invention will be better understood by the following Examples.

Example 1

| Components | w/v % |
| --- | --- |
| (1) isopropyl myristate | 2.0 |
| (2) propylene glycol | 1.5 |
| (3) squalane | 1.0 |
| (4) P.O.E(10) octylphenyl ether (Nikko Chemicals Co., Ltd.: OP-10) | 1.2 |
| (5) sodium P.O.E(3) lauryl ether sulfate | 0.2 |
| (6) ethanol | 3.0 |
| (7) purified water | 11.0 |
| (8) n-butane gas | residual quantity |
| | 100.0 |

The components (1)–(5) were mixed together and heated to 50° C. to dissolve the components into each other. The obtained solution and the components (6) and (7) were introduced together into a pressure vessel, after which a valve was set on the vessel. Subsequently, the component (8) was injected into the vessel under pressure, after which the vessel was shaken to obtain a cracking foam preparation of the present invention.

Example 2

| Components | w/v % |
| --- | --- |
| (1) isopropyl myristate | 2.0 |
| (2) 2-octyldodecanol | 1.0 |
| (3) 1,3-butylene glycol | 1.0 |
| (4) squalane | 0.5 |
| (5) P.O.E(10) octylphenyl ether (Nikko Chemicals Co., Ltd.: OP-10) | 0.8 |
| (6) sodium P.O.E(3) lauryl ether sulfate | 0.1 |
| (7) ethanol | 2.0 |
| (8) purified water | 12.0 |
| (9) n-butane gas | residual quantity |
| | 100.0 |

The components (1)–(6) were mixed together and heated to 50° C. to dissolve the components into each other. The obtained solution and the components (7) and (8) were introduced together into a pressure vessel, after which a valve was set on the vessel. Subsequently, the component (9) was injected into the vessel under pressure, after which the vessel was shaken to obtain a cracking foam preparation of the present invention.

Example 3

| Components | w/v % |
| --- | --- |
| (1) octyldodecyl myristate | 3.0 |
| (2) 3-methyl-1,3-butanediol | 1.0 |
| (3) liquid paraffin | 1.0 |
| (4) cholesterol | 0.2 |
| (5) P.O.E(10) octylphenyl ether (Nikko Chemicals Co.. Ltd.: OP-10) | 1.0 |
| (6) ethanol | 2.5 |
| (7) purified water | 11.0 |
| (8) n-butane gas | residual quantity |
| | 100.0 |

The components (1)–(5) were mixed together and heated to 50° C. to dissolve the components into each other. The obtained solution and the components (6)

and (7) were introduced together into a pressure vessel, after which a valve was set on the vessel. Subsequently, the component (8) was injected into the vessel under pressure, after which the vessel was shaken to obtain a cracking foam preparation of the present invention.

| Example 4 | |
|---|---|
| Components | w/v % |
| (1) α-menthol | 0.3 |
| (2) squalane | 1.5 |
| (3) 1,3-butanediol | 1.5 |
| (4) P.O.E(10) octylphenyl ether (Nikko Chemicals Co., Ltd.: OP-10) | 0.8 |
| (5) perfume | 0.1 |
| (6) talc | 0.5 |
| (7) ethanol | 3.0 |
| (8) purified water | 9.4 |
| (9) n-butane gas | residual quantity |
| | 100.0 |

The components (1)–(5) were mixed together and heated to 50° C. to dissolve the components each other. The obtained solution and the components (6) and (8) were introduced together into a pressure vessel, after which a valve was set on the vessel. Subsequently, the component (9) was injected into the vessel under pressure, after which the vessel was shaken to obtain a body cologne cracking foam preparation of the present invention.

| Example 5 | |
|---|---|
| Components | w/v % |
| (1) α-menthol | 3.0 |
| (2) methyl salicylate | 1.0 |
| (3) eucalyptus oil | 0.5 |
| (4) 1,3-butanediol | 0.5 |
| (5) squalane | 0.1 |
| (6) cholesterol | 0.1 |
| (7) P.O.E(10) octylphenyl ether (Nikko Chemicals Co., Ltd.: OP-10) | 1.0 |
| (8) talc | 1.0 |
| (9) ethanol | 8.0 |
| (10) purified water | 10.0 |
| (11) n-butane gas | residual quantity |
| | 100.0 |

The components (1)–(7) were mixed together and heated to 50° C. to dissolve the components each other. The obtained solution and the components (8)–(10) were introduced together into a pressure vessel, after which a valve was set on the vessel. Subsequently, the component (11) was injected into the vessel under pressure, after which the vessel was shaken to obtain a cracking mousse preparation containing an anti-inflammatory, analgesic agent of the present invention.

| Example 6 | |
|---|---|
| Components | w/v % |
| (1) α-menthol | 3.0 |
| (2) methyl salicylate | 0.5 |
| (3) peppermint oil | 0.5 |
| (4) propylene glycol | 1.0 |
| (5) P.O.E(15) octylphenyl ether (Daiichi Pharmaceutical Co., Ltd.: Noigen EA 152) | 0.8 |
| (6) P.O.E POP glycol (Nippon Oil & Fats Co., Ltd.: 70DP-950B) | 0.05 |
| (7) talc | 1.0 |
| (8) ethanol | 2.5 |
| (9) purified water | 12.0 |
| (10) n-butane gas | residual |

| Example 6 -continued | |
|---|---|
| Components | w/v % |
| | quantity |
| | 100.00 |

The components (1)–(6) were mixed together and heated to 50° C. to dissolve the components each other. The obtained solution and the components (7)–(9) were introduced together into a pressure vessel, after which a valve was set on the vessel. Subsequently, the component (10) was injected into the vessel under pressure, after which the vessel was shaken to obtain a cracking mousse preparation containing an anti-inflammatory, analgesic agent of the present invention.

| Example 7 | |
|---|---|
| Components | w/v % |
| (1) α-menthol | 3.0 |
| (2) methyl salicylate | 1.0 |
| (3) eucalyptus oil | 0.3 |
| (4) 1,3-butanediol | 0.2 |
| (5) squalane | 0.2 |
| (6) cholesterol | 0.1 |
| (7) P.O.E(10) octylphenyl ether (Nikko Chemicals Co., Ltd.: OP-10) | 0.8 |
| (8) perfume | trace amount |
| (9) talc | 1.0 |
| (10) sodium P.O.E(3) lauryl ether sulfate (Nikko Chemicals Co., Ltd.: SBL-3N-27) | 0.3 |
| (11) ethanol | 3.0 |
| (12) purified water | 11.0 |
| (13) n-butane gas | residual quantity |
| | 100.0 |

The components (1)–(8) were mixed together and heated to 50° C. to dissolve the components each other. The obtained solution and the components (9)–(12) were introduced together into a pressure vessel, after which a valve was set on the vessel. Subsequently, the component (13) was injected into the vessel under pressure, after which the vessel was shaken to obtain a cracking foam preparation containing an anti-inflammatory, analgesic agent of the present invention.

| Example 8 | |
|---|---|
| Components | w/v % |
| (1) α-menthol | 2.0 |
| (2) glycol salicylate | 0.5 |
| (3) 1,3-butanediol | 1.0 |
| (4) squalane | 0.3 |
| (5) cholesterol | 0.1 |
| (6) P.O.E(10) octylphenyl ether (Nikko Chemicals Co., Ltd.: OP-10) | 0.8 |
| (7) talc | 0.5 |
| (8) sodium P.O.E(3) lauryl ether sulfate (Nikko Chemicals Co., Ltd.: SBL-3N-27) | 0.2 |
| (9) carboxyvinyl polymer | 0.02 |
| (10) ethanol | 0.3 |
| (11) purified water | 12.1 |
| (12) n-butane gas | residual quantity |
| | 100.0 |

The components (1)–(6) were mixed together and heated to 50° C. to dissolve the components each other and to obtain an oily solution. The component (9) was incorporated with the components (10) and (11) and then stirred to swell the component (9) in the components (10) and (11) and to obtain a swelling mixture. The swelling mixture, the oily solution and the components (7) and (8) were introduced together into a pressure vessel, after which a valve was set on the vessel. Subsequently, the component (12) was injected into the vessel under pressure, after which the vessel was shaken to obtain a cracking foam preparation containing an anti-inflammatory, analgesic agent of the present invention.

| Example 9 | |
|---|---|
| Components | w/v % |
| (1) l-menthol | 2.0 |
| (2) methyl salicylate | 0.5 |
| (3) tocopherol acetate | 0.3 |
| (4) methylpolysiloxane | 0.1 |
| (5) squalane | 0.2 |
| (6) cholesterol | 0.1 |
| (7) P.O.E(10) octylphenyl ether (Nikko Chemicals Co., Ltd.: OP-10) | 1.0 |
| (8) perfume | trace amount |
| (9) talc | 1.0 |
| (10) sodium P.O.E (3) lauryl ether sulfate (Nikko Chemicals Co., Ltd.: SBL-3N-27) | 0.5 |
| (11) ethanol | 3.0 |
| (12) purified water | 11.0 |
| (13) n-butane gas | residual quantity |
| | 100.0 |

The components (1)–(8) were mixed together and heated to 50° C. to dissolve the components each other. The obtained solution and the components (9)–(12) were introduced together into a pressure vessel, after which a valve was set on the vessel. Subsequently, the component (13) was injected into the vessel under pressure, after which the vessel was shaken to obtain a cracking foam preparation containing an anti-inflammatory, analgesic agent of the present invention.

| Example 10 | |
|---|---|
| Components | w/v % |
| (1) l-menthol | 2.0 |
| (2) dl-camphor | 3.0 |
| (3) tocopherol acetate | 0.3 |
| (4) methylpolysiloxane | 0.1 |
| (5) crotamiton | 0.5 |
| (6) cholesterol | 0.1 |
| (7) P.O.E(10) octylphenyl ether (Nikko Chemicals Co., Ltd.: OP-10) | 1.0 |
| (8) perfume | trace amount |
| (9) talc | 1.0 |
| (10) sodium P.O.E (3) lauryl ether sulfate (Nikko Chemicals Co., Ltd.: SBL-3N-27) | 0.5 |
| (11) ethanol | 3.0 |
| (12) purified water | 11.0 |
| (13) n-butane gas | residual quantity |
| | 100.0 |

The components (1)–(8) were mixed together and heated to 50° C. to dissolve the components each other. The obtained solution and the components (9)–(12) were introduced together into a pressure vessel, after which a valve was set on the vessel. Subsequently, the component (13) was injected into the vessel under pressure, after which the vessel was shaken to obtain a cracking foam preparation containing an anti-inflammatory, analgesic agent of the present invention.

| Example 11 | |
|---|---|
| Components | w/v % |
| (1) clobetasol 17-propionate | 0.05 |
| (2) tocopherol acetate | 0.3 |
| (3) chlorhexidine hydrochloride | 0.1 |
| (4) 1,3-butanediol | 0.2 |
| (5) crotamiton | 1.0 |
| (6) cholesterol | 0.1 |
| (7) P.O.E(10) octylphenyl ether (Nikko Chemicals Co., Ltd.: OP-10) | 1.0 |
| (8) sodium P.O.E (3) lauryl ether sulfate (Nikko Chemicals Co., Ltd.: SBL-3N-27) | 0.5 |
| (9) talc | 0.5 |
| (10) ethanol | 2.5 |
| (11) purified water | 12.6 |
| (12) n-butane gas | residual quantity |
| | 100.00 |

The components (1)–(7) were mixed together and heated to 50° C. to dissolve the components each other. The obtained solution and the components (8)–(11) were introduced together into a pressure vessel, after which a valve was set on the vessel. Subsequently, the component (12) was injected into the vessel under pressure, after which the vessel was shaken to obtain a cracking foam preparation containing an anti-inflammatory agent of the present invention.

| Example 12 | |
|---|---|
| Components | w/v % |
| (1) l-menthol | 2.0 |
| (2) glycol salicylate | 1.0 |
| (3) indometacin | 0.5 |
| (4) 1,3-butanediol | 0.2 |
| (5) crotamiton | 0.5 |
| (6) cholesterol | 0.1 |
| (7) P.O.E(10) octylphenyl ether (Nikko Chemicals Co., Ltd.: OP-10) | 1.0 |
| (8) sodium P.O.E(3) lauryl ether sulfate (Nikko Chemicals Co., Ltd.: SBL-3N-27) | 0.5 |
| (9) carboxyvinyl polymer | 0.05 |
| (10) ethanol | 2.5 |
| (11) purified water | 12.6 |
| (12) n-butane gas | residual quantity |
| | 100.00 |

The components (1)–(7) were mixed together and heated to 50° C. to dissolve the components each other and to obtain an oily solution. The component (9) was incorporated with the components (10) and (11) and then stirred to swell the component (9) in the components (10) and (11) and to obtain a swelling mixture. The swelling mixture, the oily solution and the component (8) were introduced together into a pressure vessel, after which a valve was set on the vessel. Subsequently, the component (12) was injected into the vessel under pressure, after which the vessel was shaken to obtain a cracking foam preparation containing an anti-inflammatory, analgesic agent of the present invention.

| Example 13 | |
|---|---|
| Components | w/v % |
| (1) l-menthol | 2.0 |
| (2) ketoprofen | 2.0 |
| (8) 1,3-butanediol | 0.5 |
| (4) crotamiton | 1.0 |
| (5) cholesterol | 0.1 |
| (6) isopropyl myristate | 0.5 |
| (7) P.O.E(10) octylphenyl ether (Nikko Chemicals Co., Ltd.: OP-10) | 1.0 |

-continued

| Example 13 | |
|---|---|
| Components | w/v % |
| (8) talc | 1.0 |
| (9) sodium P.O.E(3) lauryl ether sulfate (Nikko Chemicals Co., Ltd.: SBL-3N-27) | 0.5 |
| (10) ethanol | 2.5 |
| (11) purified water | 11.3 |
| (12) 1N NaOH | 2.0 |
| (13) n-butane gas | residual quantity |
| | 100.0 |

The components (1)–(7) were mixed together and heated to 50° C. to dissolve the components each other. The obtained solution and the components (8)–(12) were introduced together into a pressure vessel, after which a valve was set on the vessel. Subsequently, the component (13) was injected into the vessel under pressure, after which the vessel was shaken to obtain a cracking foam preparation containing an anti-inflammatory, analgesic agent of the present invention.

| Example 14 | |
|---|---|
| Components | w/v % |
| (1) l-menthol | 0.2 |
| (2) 1,3-butanediol | 0.5 |
| (3) isopropyl myristate | 1.0 |
| (4) cholesterol | 0.1 |
| (5) squalane | 0.3 |
| (6) P.O.E(10) octylphenyl ether (Nikko Chemicals Co., Ltd.: OP-10) | 1.0 |
| (7) clotrimazole | 1.0 |
| (8) talc | 0.5 |
| (9) sodium P.O.E(3) lauryl ether sulfate (Nikko Chemicals Co., Ltd.: SBL-3N-27) | 0.5 |
| (10) ethanol | 2.5 |
| (11) purified water | 12.6 |
| (12) n-butane gas | residual quantity |
| | 100.0 |

The components (1)–(6) were mixed together and heated to 50° C. to dissolve the components each other. The obtained solution and the components (7)–(10) were introduced together into a pressure vessel, after which a valve was set on the vessel. Subsequently, the component (12) was injected into the vessel under pressure, after which the vessel was shaken to obtain a cracking foam preparation containing an antibacterial agent of the present invention.

| Example 15 | |
|---|---|
| Components | w/v % |
| (1) l-menthol | 0.5 |
| (2) camphor | 0.5 |
| (8) methyl salicylate | 0.5 |
| (4) diphenhydramine | 0.2 |
| (5) 1,3-butanediol | 0.3 |
| (6) cholesterol | 0.1 |
| (7) P.O.E(10) octylphenyl ether (Nikko Chemicals Co., Ltd.: OP-10) | 1.0 |
| (8) talc | 0.5 |
| (9) ethanol | 2.5 |
| (10) purified water | 11.6 |
| (11) n-butane gas | residual quantity |
| | 100.0 |

The components (1)–(7) were mixed together and heated to 50° C. to dissolve the components each other. The obtained solution and the components (8)–(10) were introduced together into a pressure vessel, after which a valve was set on the vessel. Subsequently, the component (11) was injected into the vessel under pressure, after which the vessel was shaken to obtain a cracking foam preparation containing an anti-itching agent of the present invention.

| Example 16 | |
|---|---|
| Components | w/v % |
| (1) l-menthol | 0.3 |
| (2) ethinylestradiol | 0.0004 |
| (3) isopropylmethylphenol | 0.05 |
| (4) tocopherol acetate | 0.2 |
| (5) 1,3-butanediol | 0.3 |
| (6) cholesterol | 0.1 |
| (7) crotamiton | 0.5 |
| (8) P.O.E(10) octylphenyl ether (Nikko Chemicals Co., Ltd.: OP-10) | 1.0 |
| (9) talc | 0.5 |
| (10) ethanol | 2.5 |
| (11) purified water | 11.2 |
| (12) n-butane gas | residual quantity |
| | 100.0000 |

The components (1)–(8) were mixed together and heated to 50° C. to dissolve the components each other. The obtained solution and the components (9)–(11) were introduced together into a pressure vessel, after which a valve was set on the vessel. Subsequently, the component (12) was injected into the vessel under pressure, after which the vessel was shaken to obtain a cracking foam preparation containing a hair-growth stimulant of the present invention.

| Referential Example 1 | |
|---|---|
| Components | w/v % |
| (1) l-menthol | 0.3 |
| (2) squalane | 0.5 |
| (3) 1,3-butanediol | 0.5 |
| (4) P.O.E(20) P.O.P(8) cetyl ether (Nikko Chemicals Co., Ltd.: PBC-44) | 0.8 |
| (5) perfume | 0.1 |
| (6) talc | 0.5 |
| (7) ethanol | 3.0 |
| (8) purified water | 9.4 |
| (9) n-butane gas | residual quantity |
| | 100.0 |

The components (1)–(5) were mixed together and heated to 50° C. to dissolve the components each other. The obtained solution and the components (6)–(8) were introduced together into a pressure vessel, after which a valve was set on the vessel. Subsequently, the component (9) was injected into the vessel under pressure, after which the vessel was shaken to obtain an aerosol preparation.

| Referential Example 2 | |
|---|---|
| Components | w/v % |
| (1) l-menthol | 3.0 |
| (2) methyl salicylate | 1.0 |
| (3) eucalyptus oil | 0.3 |
| (4) 1,3-butanediol | 0.2 |
| (5) squalane | 0.2 |
| (6) cholesterol | 0.1 |
| (7) P.O.E(20) P.O.P(8) cetyl ether (Nikko Chemicals Co., Ltd.: PBC-44) | 1.0 |
| (8) perfume | trace amount |
| (9) talc | 1.0 |
| (10) ethanol | 3.0 |
| (11) purified water | 12.5 |
| (12) n-butane gas | residual quantity |

-continued

| Referential Example 2 | |
|---|---|
| Components | w/v % |
| | 100.0 |

The components (1)–(8) were mixed together and heated to 50° C. to dissolve the components each other. The obtained solution and the components (9)–(11) were introduced together into a pressure vessel, after which a valve was set on the vessel. Subsequently, the component (12) was injected into the vessel under pressure, after which the vessel was shaken to obtain an aerosol preparation containing an anti-inflammatory, analgesic agent.

| Referential Example 3 | |
|---|---|
| Components | w/v % |
| (1) l-menthol | 2.0 |
| (2) glycol salicylate | 0.5 |
| (3) 1,3-butanediol | 1.0 |
| (4) squalane | 0.3 |
| (5) cholestrol | 0.1 |
| (6) P.O.E(20) P.O.P(8) cetyl ether (Nikko Chemicals Co., Ltd.: PBC-44) | 1.0 |
| (7) carboxyvinyl polymer | 0.02 |
| (8) ethanol | 3.0 |
| (9) purified water | 12.1 |
| (10) n-butane gas | residual quantity |
| | 100.00 |

The components (1)–(6) were mixed, together and heated to 50° C. to dissolve the components each other and to obtain an oily solution. The component (7) was incorporated with the components (8) and (9) and then stirred to swell the component (7) in the components (8) and (9) and to obtain a swelling mixture. The swelling mixture and the oily solution were introduced together into a pressure vessel, after which a valve was set on the vessel. Subsequently, the component (10) was injected into the vessel under pressure, after which the vessel was shaken to obtain an aerosol preparation containing an anti-inflammatory, analgesic agent.

| Referential Example 4 | |
|---|---|
| Components | w/v % |
| (1) l-menthol | 3.0 |
| (2) methyl salicylate | 1.0 |
| (3) eucalyptus oil | 0.3 |
| (4) 1,3-butanediol | 0.2 |
| (5) squalane | 0.2 |
| (6) cholesterol | 0.1 |
| (7) P.O.E(10) octylphenyl ether (Nikko Chemicals Co., Ltd.: OP-10) | 0.8 |
| (8) ethanol | 3.0 |
| (9) purified water | 12.0 |
| (10) liquefied petroleum gas (a mixture of propane 2 wt. %, isobutane 28 wt. % and n-butane 70 wt. %) | residual quantity |
| | 100.00 |

The components (1)–(7) were mixed together and heated to 50° C. to dissolve the components each other. The obtained solution and the components (8) and (9) were introduced together into a pressure vessel, after which a valve was set on the vessel. Subsequently, the component (10) was injected into the vessel under pressure, after which the vessel was shaken to obtain an aerosol preparation containing an anti-inflammatory, analgesic agent.

| Referential Example 5 | |
|---|---|
| Components | w/v % |
| (1) l-menthol | 3.0 |
| (2) methyl salicylate | 1.0 |
| (3) eucalyptus oil | 0.3 |
| (4) 1,3-butanediol | 4.0 |
| (5) ethanol | 26.0 |
| (6) purified water | 22.0 |
| (7) talc | 3.0 |
| (8) dimethyl ether | 12.0 |
| (9) liquefied petroleum gas (a mixture of dimethyl ether 60 wt. %, propane 2 wt. %, isobutane 15 wt. % and n-butane 23 wt. %) | residual quantity |
| | 100.00 |

The component (1) was incorporated with the components (2)–(5), dissolved therein and then incorporated with the component (6), after which the whole was stirred and then introduced together with the component (7) into a pressure vessel on which a valve was set after the introduction. Subsequently, the components (8) and (9) were injected into the vessel under pressure thereby to obtain an aerosol preparation containing an anti-inflammatory, analgesic agent.

Experiment 1

The cracking foam preparations of Examples 1 to 3 and the aerosol preparations of Referential Examples 1 to 4 were each sprayed upon the forearm of a healthy man to observe the state of foaming. Further, the foam was applied by hands to evaluate the cracking sound generated by the breakage of the bubbles. The results are given in Table 1.

TABLE 1

| Evaluation of cracking foam preparations | | |
|---|---|---|
| Preparation of | State of foaming | Cracking sound |
| Example 1 | ○ | ○ |
| Example 2 | ○ | ○ |
| Example 3 | ○ | ○ |
| Referential Example 1 | X | Δ |
| Referential Example 2 | X | Δ |
| Referential Example 3 | X | Δ |
| Referential Example 4 | X | X |

(Evaluation criteria)
(1) State of foaming
○: the foam is fine and swollen
Δ: the foam is rough and disappears soon.
X: no foam is generated.
(2) Cracking sound
○: loud sound with the breakage of bubbles
Δ: faint sound
X: no sound As apparent from the results given in Table 1, the cracking foam preparations of Examples 1 to 3 according to the present invention are superior to the aerosol preparations of Referential Examples 1 to 4 containing the conventional surfactants in respect of the state of foaming and cracking sound.

Experiment 2

The cracking foam preparation of Example 5 and the aerosol preparation of Referential Example 5 were each sprayed upon the forearm of a healthy adult man for 2 seconds through a hole having a diameter of about 5 cm provided on a paper sheet to determine the skin temperature change with a thermography since spraying. The results are given in FIG. 1.

As apparent from the results given in FIG. 1, the cracking foam preparation of Example 5 is more effective in chilling the skin instantaneously than the aerosol preparation of Referential Example 5, thus being excellent as an anti-inflammatory, analgesic preparation.

Industrial Applicability

The foamable aerosol preparations of the present invention foam very well and are excellent in cracking sound when applied to the skin, despite of the use of n-butane gas as the propellant. Further, the preparations of the present invention are particularly useful from the view-point of environmental protection, because they are free from the problem of the depletion of the ozonosphere by virtue of the use of n-butane gas as the propellant instead of fluorocarbon gas heretofore used.

Furthermore, the foamable aerosol preparations containing an anti-inflammatory, analgesic agent according to the present invention contain a large amount of the gas which can be effectively incorporated into bubbles. Therefore, the preparations of the present invention are improved in the chilling effect exhibited when sprayed upon the skin as compared with conventional aerosol preparations containing an anti-inflammatory, analgesic agent, thus being excellent in anti-inflammatory and analgesic effects.

As described above, the foamable aerosol preparations of the present invention are applicable to cosmetics, quasi drugs, drugs and the like, thus being industrially useful.

We claim:

1. A foamable aerosol preparation comprising 0.1 to 5 wt./vol. % of at least one surfactant which is a member selected from the group consisting of polyoxyethylene octyl phenyl ether and sodium polyoxyethylene lauryl ether sulfate and mixtures thereof, 0.05 to 10 wt./vol. % of at least one member selected from the group consisting of ethanol, isopropanol, propylene glycol, 1,3-butanediol, 3-methyl-1,3-butanediol, dipropylene glycol, tripropylene glycol, glycerin, polyoxyethylene polyoxypropylene glycol and polyethylene glycol; 3 to 25 wt./vol. % of water and 60 to 95 wt./vol. % of n-butane gas.

2. The preparation according to claim 1, further comprising at least one powdery material selected from the group consisting of talc, powdered silicon, powdered polystyrene and silica.

3. The preparation according to claim 1, further comprising at least one oil-phase component selected from the group consisting of isopropyl palmitate, isopropyl myristate, diisopropyl sebacate, diethyl sebacate, diisopropyl adipate, glycerol caprylate, 2-octyldodecanol, 2-hexyldecanol, oleyl alcohol, squalane, liquid paraffin, isoparaffin, crotamiton and benzyl alcohol.

4. The preparation according to claim 3, wherein said oil phase component is isopropyl myristate.

5. A foamable aerosol preparation comprising (i) a base which comprises 0.1 to 5 wt./vol. % of at least one surfactant selected from the group consisting of polyoxyethylene octylphenyl ether and sodium polyoxyethylene lauryl ether sulfate and mixtures thereof, 0.05 to 10 wt./vol. % of at least one member selected from the group consisting of ethanol, isopropanol, propylene glycol, 1,3-butanediol, 3-methyl-1,3-butanediol, dipropylene glycol, tripropylene glycol, glycerin, polyoxyethylene polyoxypropylene glycol and polyethylene glycol; 3 to 25 wt./vol. % of water and 60 to 95 wt./vol. % of n-butane gas; and (ii) an active ingredient.

6. The preparation according to claim 5, further comprising at least one oil-phase component selected from the group consisting of isopropyl palmitate, isopropyl myristate, diisopropyl sebacate, diethyl sebacate, diisopropyl adipate, glycerol caprylate, 2-octyldodecanol, 2-hexyldecanol, oleyl alcohol, squalane, liquid paraffin, isoparaffin, crotamiton and benzyl alcohol.

7. The preparation according to claim 5, further comprising at least one powdery material selected from the group consisting of talc, powdered silicon, powdered polystyrene and silica.

8. The preparation according to claim 5, wherein said active ingredient is in the amount of 0.0001–12 w/v. %.

9. The preparation according to claim 8, wherein said active ingredient is a member selected from the group of antiinflammatory agents, antibacterial agents, hair-growth stimulants, antiallergic agents and insectifuges.

10. The preparation according to claim 8, wherein said active ingredient is at least one member selected from the group consisting of cholesterol, l-menthol, eucalyptus oil, methyl salicylate, peppermint oil, glycol salicylate, tocopherol acetate, clobetasol 17-propionate, indometacin, ketoprofen, clotrimazole, diphenhydramine, camphor and ethinylestradiol.

* * * * *